United States Patent [19]

Hewett et al.

[11] 4,264,626
[45] Apr. 28, 1981

[54] BENZO-BICYCLONOENE-DERIVATIVES AS ANORECTANTS AND TO TREAT DEPRESSION

[75] Inventors: Colin L. Hewett; David S. Savage, both of Glasgow, Scotland

[73] Assignee: Akzona Incorporated, Asheville, N.C.

[21] Appl. No.: 17,894

[22] Filed: Mar. 6, 1979

Related U.S. Application Data

[60] Division of Ser. No. 866,116, Dec. 30, 1977, which is a continuation of Ser. No. 735,286, Oct. 26, 1976, Pat. No. 4,107,206, which is a continuation-in-part of Ser. No. 563,435, Mar. 31, 1975, Pat. No. 4,008,277.

[30] Foreign Application Priority Data

Apr. 8, 1974 [GB] United Kingdom ............... 15558/74

[51] Int. Cl.³ ..................... A61K 31/135; C07C 87/29
[52] U.S. Cl. .................................... 424/330; 564/221; 564/427
[58] Field of Search ..................... 260/570.9, 570.8 R, 260/501.7, 501.8; 424/330

[56] References Cited

U.S. PATENT DOCUMENTS 3,836,670  9/1974  Freed .................................... 424/330

OTHER PUBLICATIONS

Chem. Abst., 72-111156m (1970).

Primary Examiner—Stanley J. Friedman
Attorney, Agent, or Firm—Robert H. Falk; Charles A. Wendel; Francis W. Young

[57] ABSTRACT

The present invention relates to novel biologically active tricyclic compounds of the general formula:

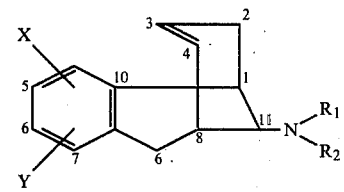

and salts thereof, in which $R_1$ and $R_2$ stand for hydrogen, alkyl or alkenyl, an optionally substituted aralkyl group or an acyl group or $R_1 + R_2$ together with the nitrogen atom represent a heterocyclic 5- or 6-membered ring, and X and Y stand for hydrogen, hydroxy, halogen, alkyl or alkoxy of 1–6 carbon atoms, nitro, trifluoromethyl or an acyloxy group, which compounds have valuable biological activities, particularly anorectic activity.

7 Claims, No Drawings

BENZO-BICYCLONOENE-DERIVATIVES AS ANORECTANTS AND TO TREAT DEPRESSION

CROSS-REFERENCE TO RELATED APPLICATION

This application is a divisional application of copending application Ser. No. 866,116 filed Dec. 30, 1977, which is a continuation of application Ser. No. 735,286 filed Oct. 26, 1976, now U.S. Pat. No. 4,107,206, which is a continuation-in-part of application Ser. No. 563,435 filed Mar. 31, 1975, now U.S. Pat. No. 4,008,277, now claiming priority from United Kingdom patent application 15,558/74 filed Apr. 8, 1974.

The present invention relates to novel biologically active tricyclic compounds, to processes for the preparation of these compounds and to the pharmaceutical application of these compounds. Particularly the invention relates to novel benzo(b)bicyclo[3.3.1]nona 3,6(10a)dienes of the general formula I:

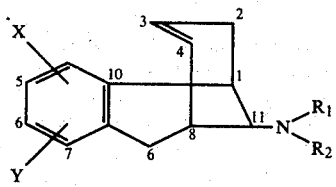

and salts thereof,
in which
$R_1$ and $R_2$ stand for hydrogen, alkyl or alkenyl, an optionally substituted aralkyl group or an acyl group or
$R_1 + R_2$ together with the nitrogen atom represent a heterocyclic 5- or 6-membered ring, and
X and Y stand for hydrogen, hydroxy, halogen, alkyl or alkoxy of 1–6 carbon atoms, nitro, trifluoromethyl or an acyloxy group.

The compounds of the general formula I have valuable biological activities, particularly anorectic activity.

Preferred compounds in this respect are those in which $R_1$ and $R_2$ stand for hydrogen or methyl and/or the benzo nucleus has been substituted by 1 or 2 halogen (Cl or Br).

A very convenient starting product in the synthesis of the compounds of formula I is a substance of the general formula II:

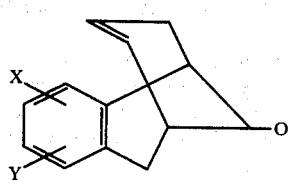

in which X and Y have the meanings indicated previously.

These compounds II may be prepared in the usual manners starting from an optionally substituted (X and/or Y) β-tetralone. The tetralone in question, which is commercially available or can be prepared in a known manner from commercially available starting products, is treated with pyrrolidine affording the corresponding 2-(pyrrolidino)enamine. The enamine is then converted with acrolein at low temperature into the corresponding 4-hydroxy-benzo(b)bicyclo[3.3.1]nonene-11-one. Alternatively the tetralone in question may be reacted directly with acrolein at elevated temperature in the presence of a tertiary amine such as triethylamine or trimethylamine to give the corresponding 4-hydroxy-benzo(b)bicyclo[3.3.1]nonene-11-one directly. The compound of formula II is obtained by tosylation of the 4-hydroxy group and removal of the tosyloxy group thus obtained in the usual manner, whereby a double bond is formed at position 3 of the molecule.

The condensation of the 2-tetralone enamine with acrolein can be carried out at preferred temperatures from −60° to +25° C. in a variety of solvents, but best conditions use a low temperature of −50° to −45° C. for the addition of acrolein and allow the temperature to increase in a controlled manner to ambient temperature over a period of up to 3 hours.

The alternative direct condensation of the optionally substituted β-tetralone with acrolein in the presence of a tertiary amine can be carried out in a variety of solvents at preferred temperatures between 30° to 120° C., but preferably at the boiling point of the solvent used.

Starting from a compound of formula II the amines or amides of the invention (I) can be prepared most conveniently and directly by a reductive amination.

This method involves a reaction of the starting ketone II with formamide, N-alkylformamide, N,N-dialkylformamide or an amine of the general formula III:

or a salt thereof, in which $R_1'$ and $R_2'$ have the same meanings as $R_1$ and $R_2$ defined before with the exception of an acyl moiety, in the presence of a reducing agent.

A reducing agent, that is very suitable for this reaction, is formic acid or a formic acid derivative such as a salt of formic acid and the amine of formula III. In the latter case the separate addition of the amine III is even superfluous. This reaction may be carried out at elevated temperature, preferably in the range of 80°–150° C., and most conveniently at the boiling point of the reaction mixture.

Other suitable reducing agents in this reaction are metal hydrides, particularly complex-metal hydrides, such as lithiumaluminiumhydride, sodiumborohydride, sodiumtrimethoxyborohydride and diisobutylaluminiumhydride, or an alkalimetal, preferably sodium, in an alcohol such as ethanol or isopropanol, used under reaction conditions whereby the isolated double bond is not or hardly attacked. This may be obtained by carrying out the reaction at the lowest possible temperature and by adding the solution or suspension of the metal hydride (or sodium) to the reaction mixture portion-wise and very slowly instead of the usual procedure of adding the reaction mixture to the solution or suspension of the metal hydride.

The compounds according to the invention can also be obtained by a reduction of the imino-moiety of a compound of the general formula IV:

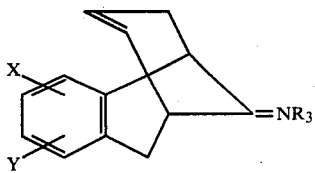

IV in which X and Y have the aforesaid meanings and $R_3$ stands for hydrogen, hydroxy, alkoxy, alkyl (1–6 C) or an optionally substituted aralkyl group.

The reduction of the imine IV is carried out under mild reaction conditions by means of standard procedures for the reduction of an imino moiety. For example, the reduction can be carried out by hydrogenation in the presence of a suitable catalyst such as Raney nickel, Pt or $PtO_2$, with a metal hydride, particularly complex-metal hydrides derived from aluminium or boron, such as lithiumaluminiumhydride, dissolved or suspended in a suitable liquid such as ether, with an alkalimetal, preferably sodium, in a suitable solvent such as ether, benzene or alcohol, or with sodiumamalgam or zinc dust in, for example, sodiumhydroxide. Obviously the reaction is carried out at the lowest possible temperature in order to avoid a reduction of the isolated double bond.

The compounds of the formula IV can be prepared by the reaction of the ketone II with a primary amine of formula III or with hydroxylamine or a hydroxylaminealkylether in the usual manner.

A third method for the preparation of the compounds according to the invention is starting from a compound of the general formula:

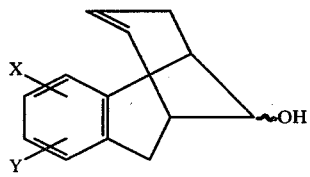

V in which X and Y have the aforementioned meanings.

The hydroxyl-compounds V are obtained by reduction of the keto group of the ketone II (into a hydroxyl group).

This reduction is carried out at relatively low temperature using suitable reducing agents, preferably metal hydrides such as sodiumborohydride, diisobutylaluminiumhydride, sodiumtrimethoxyborohydride, lithiumaluminiumhydride, etc.

The hydroxyl-compound V can be converted into the corresponding amine in various ways. For example, the said hydroxyl group may be converted into a leaving group, such as a mesyloxy group, a tosyloxy group, a p-bromophenyl- or p-chlorophenyl-sulphonyloxy group, a 2-tetrahydropyranyloxy group, etc., and then be reacted with an amine according to the general formula III.

Instead of the conversion of the hydroxyl group into an abovementioned etherified or esterified hydroxyl group as leaving group, the hydroxyl group may also be halogenated, for example with $PCl_5$, $PBr_3$, $SOCl_2$, etc., and the halogenated compound thus obtained be converted into the desired compound I by reaction with the amine III.

The conversion from a hydroxyl group into an amino group are well-known and described in any chemical handbook.

The aforesaid primary reactions for the preparation of the compounds of the invention (I) may be followed by additional reactions for the conversion of a compound of formula I into a functional derivative, such as a salt, or for the conversion from one compound of the invention into another compound of the invention.

So, it is possible to modify a substituent present at the phenylnucleus into another substituent within the definition of X and/or Y. For example, a methoxy group may be converted into a hydroxyl group, e.g. by treating with fused pyridine.HCl in the absence of a solvent or by hydrolysis with HBr; a hydroxy group can be converted into an alkoxy group, halogen, or an acyloxy group in a conventional manner.

The amines of the invention, unsubstituted or monosubstituted at the nitrogen atom ($R_1$ and/or $R_2$ is hydrogen), may be (ar)alkylated in the usual manner, for example by reacting the compound with an (ar)alkylhalide, or by acylating the compound followed by reduction of the carbonyl group.

For the introduction of methyl-groups at the nitrogen atom the well-known procedure of Eschweiler-Clarke (reaction with formaldehyde + formic acid) or the reaction with formaldehyde or haloformic esters, followed by reduction with e.g. sodiumcyanoborohydride is to be preferred.

An acyl derivative of the compounds according to the invention, in which at least one of the groups $R_1$ or $R_2$ is hydrogen may be obtained by acylating the compound in the usual manner, preferably by using an anhydride or acid halide.

Where an N-formyl derivative I is obtained directly from one of the aforesaid primary reactions, the amide in question may be hydrolysed using e.g. potassium or sodiumhydroxide to obtain the primary amine I. For example, the reductive amination, in which the ketone II is reacted with formamide in the presence of formic acid (Leuckart-Wallach reaction), results in first instance in the N-formyl derivative I, which derivative can be hydrolysed to the primary amine I, or reduced to the corresponding N-methyl compound I.

All these additional conversions which might be carried out after the aforesaid primary reactions are standard procedures well-known in the art. As far as specific reagents have been mentioned in these additional conversions, it may be understood that these reagents can be replaced by other reagents, well-known in organic chemistry, having a similar effect as the specific reagents described.

The preparation of the ketone II used as starting product in the present synthesis to a compound of formula I results in a racemic mixture consisting of two enantiomers of formula II. This racemic mixture II may be processed into the racemic mixture of formula I or the racemic mixture II can be resolved into the separate enantiomers II in a conventional manner whereupon the separate enantiomers are converted into an optically active endproduct according to formula I.

The replacement of the oxo group at position 11 of the ketone of formula II with an amino group introduces another asymmetric centre resulting into a mixture of two diastereoisomers I, in which the amino group is present in syn- or anti-position with respect to the benzene ring. The separate diastereo-isomeric forms can be isolated from the mixture in the usual manner, for example by column chromatography, preparative thin-layer chromatography and/or fractional crystallisation.

As described previously, one of the primary methods for the preparation of the compounds of the invention involves in first instance a reduction of the oxo group of the ketone II into the corresponding hydroxyl-compound. It may be understood that this reduction results in a mixture of diastereoisomers, in which the hydroxyl group is present in syn- and in anti-position. This mixture can be converted into a mixture of the syn-amino and anti-amino compound of formula I or the mixture can be separated into the separate diastereoisomeric hydroxyl compounds and then be processed into the syn- or anti-amino compound I. The conversion of the hydroxyl group, for example in syn-position, into an amino group in the manner described before generally involves a complete inversion of the configuration. In other words a syn-hydroxyl compound affords, in general, an anti-amino compound I.

The diastereoisomers, enantiomers and mixtures thereof as well as their preparation are also encompassed by this invention.

The novel compounds of formula I may be isolated from the reaction mixture in the form of pharmaceutically acceptable salts, dependent upon the conditions in which the reaction is carried out. The pharmaceutically acceptable salts may also be obtained by treating the free base I with an organic or inorganic acid such as HCl, HBr, HI, $H_2SO_4$, $H_3PO_4$, acetic acid, propionic acid, glycollic acid, maleic acid, malonic acid, succinic acid, tartaric acid, citric acid, benzoic acid, ascorbic acid, etc.

The term "alkyl" used in the definition of X, Y, $R_1$ and $R_2$ of the general formula I means a saturated branched or unbranched hydrocarbon (including cyclohydrocarbon) radical with 1-6 carbon atoms, such as methyl, ethyl, n.propyl, n.butyl, cyclopropyl, methylcyclopropyl, cyclobutyl, methylcyclobutyl, isopropyl, isobutyl, t.butyl, n-pentyl, isopentyl, cyclopentyl and hexyl. The same applies to the alkyl group present in the term "alkoxy" used in the definition of X and Y.

By "alkenyl" is meant an unsaturated alkyl group with 2-6 carbon atoms, such as allyl, (2)butenyl, etc.

With an "aralkyl group", mentioned in the definition of $R_1$ and $R_2$ is meant an alkyl group with 1-6 carbon atoms, substituted with at least one aromatic group. Preferably a phenylalkyl group is meant, in which the alkyl group has 1-4 carbon atoms and in which the phenyl group may optionally be substituted by one or more hydroxy, halogen, lower alkyl or alkoxy groups (1-4 C), such as benzyl, phenylethyl, phenylpropyl, phenylbutyl, 1-methyl-1-phenyl-ethyl, o-, m-, or p-anisyl, o-, m- or p-chloro-benzyl, veratryl, o-, m- or p-methyl-phenethyl, o-, m- or p-hydroxy-phenethyl, etc.

An "acyl group" mentioned in the definition of $R_1$ and $R_2$ means a group derived from an aliphatic, araliphatic or aromatic carboxylic acid. The aliphatic carboxylic acids cover acids with 1-18 carbon atoms, including a carbocyclic ring, and particularly those with 1-8 carbon atoms, such as acetic acid, propionic acid, butyric acid, iso-butyric acid, valeric acid, hexanoic acid, heptanoic acid, trimethyl-acetic acid, cyclopentane-carboxylic acid and cyclohexane-carboxylic acid. The araliphatic or aromatic carboxylic acids cover optionally substituted araliphatic or aromatic carboxylic acids with 7-18 carbon atoms, especially the optionally substituted phenyl-carboxylic acids and optionally substituted phenylalkyl-carboxylic acids, in which the alkyl group contains 1-4 carbon atoms and may be saturated as well as unsaturated, such as benzoic acid, o-, m- or p-toluic acid, o- or p-chlorobenzoic acid, p-methoxybenzoic acid, phenyl-acetic acid, phenylpropionic acid, cinnamic acid, phenylbutyric acid, p-methylphenyl-acetic acid, etc.

The acyl group in the term "acyloxy" used in the definition of X and Y has a similar meaning.

The heterocyclic five- or six-membered rings, as mentioned in the definition of $R_1$ and $R_2$ (together with the nitrogen atom), are derived from 5- or 6-membered cyclic amines of the general formula III, such as pyrrole, pyrrolidine, pyrroline, piperidine, piperazine, imidazole or morpholine.

The novel compounds according to this invention as well as the pharmaceutically acceptable salts thereof have, as already said, valuable anorectic activities. For example 8-chloro-11-amino-benzo(b)bicyclo[3.3.1]nona-3,6a(10a)-diene.HCl is a potent anorectic agent in several animal species. In contrast to other known anorectic compounds a long term oral administration of this compound did not evoke tolerance to its anorectic effect.

Furthermore an antidepressant effect is indicated by the overall pharmacological profile of the compounds of the invention.

The compounds of the invention may be administered orally or parenterally, in a daily dosage of from 0.005-50 mg, preferably 0.01-10 mg per kg body weight.

Mixed with suitable auxiliaries the compounds I may be compressed into solid dosage units, such as pills, tablets and coated tablets or be processed into capsules.

By means of suitable liquids the compounds I can also be applied as an injection preparation in the form of solutions, suspensions or emulsions.

STARTING PRODUCTS

The preparation of benzo(b)bicyclo[3.3.1]nona-3,6a(10a)dien-11-one is described starting from β-tetralone. Other starting products according to formula II are prepared in a similar manner.

A. β-tetralone pyrrolidine enamine

A mixture of β-tetralone (500 g), benzene (3 l) and pyrrolidine (400 ml) was refluxed under nitrogen for 2 h using a Dean and Stark water separator to collect the water formed. The reaction mixture was evaporated to dryness under reduced pressure, venting with nitrogen at the end of the distillation. The residue was crystallised from light petroleum to give β-tetralone pyrrolidine enamine (680 g; 87%) m.p. 80°–83° C.

B. 4-hydroxy-benzo(b)-bicyclo[3.3.1]nonen-11-one

B.1. A suspension of β-tetralone pyrrolidine-enamine (100 g) in sodium-dried ether (700 ml) was cooled to −7° C.±2° under nitrogen, and a solution of acrolein (50 ml) in dry ether (50 ml) was added dropwise over 30 min with stirring, while allowing the temperature to rise to 0° C.±2° over 45 min.

Further additions of acrolein (25 ml, 15 ml and 10 ml) in equal volumes of ether were added at hourly intervals, each addition taking 20 min, keeping the temperature at 0° C.±2° throughout. After 5 h, water (200 ml) was added dropwise while maintaining the temperature at 0° to 5° C. After a further half hour 5 N hydrochloric acid (100 ml) was added dropwise to pH 3–6, maintaining the temperature at 5° C.±2°. The product was extracted into methylene chloride, (2×250 ml) and the extract was washed with water to pH 7, dried and filtered through silica gel.

Crystallisation from methylene chloride/ether gave 4-hydroxy-benzo(b)bicyclo[3.3.1]nonen-11-one (50 g) as a mixture of 4-exo- and endo-hydroxy epimers. The compound B may also be prepared as follows:

B.2. β-Tetralone pyrrolidine-enamine (100 g) was added to a stirred, freshly prepared solution of acrolein (55 ml) in methylene chloride (1 l) at −55° to −60° C. After stirring for 30 min at −60° the temperature of the solution was allowed to rise to −12°±2° C. over 30 min. After ½ h the reaction temperature was allowed to rise to −5° over a further ½ h (total reaction time 2 h) and water (100 ml) was added. The organic layer was separated off and washed with 1 N hydrochloric acid (3×250 ml) and water (2×250 ml) to pH 7, and dried.

The dried extracts were concentrated, slaked with ether, and the crude product (76 g) was recrystallised from methanol to give 4-exo-hydroxy-benzo(b)bicyclo[3.3.1]nonen-11-one (54 g) m.p. 149°–152° C.

C. benzo(b)-bicyclo[3.3.1]nona-3,6a(10a)-dien-11-one

A solution of 4-exo- and 4-endo-hydroxy-benzo(b)bicyclo[3.3.1]nonan-11-one (100 g B) in pyridine (250 ml) was cooled with stirring to 5° C.±2° and methane sulphonyl chloride (78 ml) was added dropwise keeping the temperature below 10° C. Stirring was continued at 5° to 10° C. for a further ½ h and the reaction was set aside at this temperature for about 72 h. The mixture was poured into ice (8 l) and allowed to stand at room temperature for 18 h. The mesylate was filtered and dissolved in methylene chloride (500 ml). After separation from the excess of water the solution was dried and evaporated to dryness (140 g). Recrystallisation from methylene chloride/ether gave the mesylate as prisms (120 g) m.p. 106°–107° C.

The mesylate from above (120 g) was dissolved in collidine (350 ml) and the mixture distilled down until the temperature reached 165°–170° C. Heating was continued under reflux for a further 5 h and the cooled solution was poured into a mixture of ice (5 l) and 5 N hydrochloric acid (300 ml). The solid was filtered off, washed and dissolved in ether (250 ml). The solution was washed with water till neutral, dried and evaporated to dryness. The residue was distilled under reduced pressure to give benzo(b)bicyclo[3.3.1]nona-3,6a(10a)-dien-11-one, b.p. 144°/2 mm Hg.

D. benzo(b)bicyclo[3.3.1]nona-3,6a(10a)-dien-11-one (tosyloxy route)

Toluene-sulphonyl chloride (175 g) was added in portions to a stirred solution of 4-exo- and 4-endo-hydroxybenzo(b)bicyclo[3.3.1]nona-3,6a(10a)diene-11-one (150 g B) in dry pyridine (300 ml) at 5° C.±2°. After ½ h the temperature was allowed to rise and the reaction was continued at room temperature for 3 days. The solution was poured into water and the product was filtered off, dissolved in methylene chloride and washed with 1 N hydrochloric acid, water to pH 7, dried and evaporated to dryness (260 g). Crystallisation from methylene chloride/ether gave a sample of the pure tosylate m.p. 150°–151° C. Lithium carbonate (260 g) and lithium bromide (55 g) were added to a solution of the tosylate (260 g) in dimethyl acetamide (2.5 l) and the mixture was slowly distilled over 2 hours, collecting about 2 liters of distillate. After cooling the residue was poured into ice and allowed to stand overnight. The solid was filtered off, digested with ether and the inorganic residue was removed by filtration. The filtrate was washed with water to pH 7, dried and evaporated to dryness. The residue was distilled under reduced pressure to give benzo(b)bicyclo[3.3.1]nona-3,6a(10a)-dien-11-one, b.p. 130°–140° C./1 mm Hg (105 g).

EXAMPLE I 11-formamido-benzo(b)bicyclo[3.3.1]-nona-3,6a(10a)diene

A solution of benzo(b)bicyclo[3.3.1]-nona-3,6a(10a)-dien-11-one (102 g) in a mixture of formamide (400 ml) and formic acid (200 ml) is boiled under reflux for 1½ h and poured into a mixture of ice and potassium hydroxide solution. After allowing to stand for 18 h, the solid is filtered off, dissolved in methylene chloride, washed neutral and chromatographed to give 11-syn-formamido-benzo(b)bicyclo[3.3.1]nona-3,6a(10a)-diene (22.5 g) in needles, m.p. 182°–183° C., and 11anti-formamido-benzo(b)bicyclo[3.3.1]nona-3,6a(10a)-diene (27.6 g), m.p. 173°–178° C.

EXAMPLE II 11-amino-benzo(b)bicyclo[3.3.1]-nona-3,6a(10a)-diene.HCl

A solution of 11-syn-formamido-benzo(b)bicyclo[3.3.1]nona-3,6a(10a)-diene (6.0 g) in ethanol (60 ml) and 10 M potassium hydroxide solution (6 ml) is boiled under reflux for 4.5 h, concentrated, and the amine precipitated by addition of an excess of water. Extraction with ether gives 11-syn-amino-benzo(b)bicyclo[3.3.1]nona-3,6a(10a)diene (6.5 g) as an oil, which is dissolved in ether and converted to the hydrochloride by addition of a solution of hydrogen chloride in ether. Crystallisation from methanol gives pure 11-syn-amino-benzo(b)bicyclo[3.3.1]nona-3,6a(10a)-diene hydrochloride (5.6 g) m.p. >280° C.

In the same manner the 11-anti-amino-benzo(b)bicyclo[3.3.1]nona-3,6a(10a)-diene.HCl is prepared (sublimation point about 265° C.) starting from the corresponding 11-anti-formamido-compound.

EXAMPLE III 8-methoxy-11-formamido-benzo(b)bicyclo[3.3.1]nona-3,6a(10a)-diene

A solution of 8-methoxy-benzo(b)bicyclo[3.3.1]nona-3,6a(10a)-dien-11-one (45 g) in formic acid (90 ml) and formamide (270 ml) is heated under reflux for 1¾ h, cooled and poured into a mixture of ice and 10 N KOH solution to give a mixture of 11-syn- and 11-anti-formamido-8-methoxy-benzo(b)bicyclo[3.3.1]nona-3,6a(10a)-diene (43 g) (approx. 45:55).

The product is dissolved in toluene, filtered through alumina and carefully chromatographed to give a separation of the 11-epimers. Crystallisation from methylene chloride/ether of combined fractions gives 8-methoxy-11-anti-formamido-benzo(b)bicyclo[3.3.1]nona-3,6a(10a)-diene (15 g) m.p. 153°–155°, and 8-methoxy-11-syn-formamido-benzo(b)bicyclo[3.3.1]nona-3,6a(10a)-diene, (14.5 g) m.p. 125°–126° C.

EXAMPLE IV 8-chloro-11-formamido-benzo(b)bicyclo[3.3.1]nona-3,6a(10a)-diene 8-chloro-benzo(b)bicyclo[3.3.1]nona-3,6a(10a)-dien-11-one (33 g) is dissolved in a mixture of formic acid (98%; 198 ml) and formamide (330 ml) and the solution refluxed for 3.5 h, cooled, diluted with water and made alkaline with 5% aqueous sodium carbonate solution. The mixture is extracted with methylene dichloride, and the extracts washed neutral with water, dried (MgSO$_4$) and evaporated to dryness yielding a mixture of 11-anti- and 11-syn-formamido-8-chloro-benzo(b)bicyclo[3.3.1]nona-3,6a(10a)-diene (37 g) as an oily substance.

EXAMPLE V 11-formamido-substituted benzo(b)bicyclo[3.3.1]nona-3,6a(10a)-diene Starting from the desired benzo(b)bicyclo[3.3.1]nona-3,6a(10a)-dien-11-one compound substituted at the phenyl ring with 8-bromo-, 8-hydroxy, 9-chloro, 8,9-dichloro, 8,10-dichloro, 8-methyl or 9-CF$_3$ respectively, the following 11-formamido compounds are prepared in the same manner as described in Example I:

8,10-dichloro-11-formamido-benzo(b)bicyclo[3.3.1]nona-3,6a(10a)-diene,
8-bromo-11-formamido-benzo(b)bicyclo[3.3.1]nona-3,6a(10a)-diene,
8-hydroxy-11-formamido-benzo(b)bicyclo[3.3.1]nona-3,6a(10a)-diene,
9-chloro-11-formamido-benzo(b)bicyclo[3.3.1]nona-3,6a(10a)-diene,
8,9-dichloro-11-formamido-benzo(b)bicyclo[3.3.1]nona-3,6a(10a)-diene,
8-methyl-11-formamido-benzo(b)bicyclo[3.3.1]nona-3,6a(10a)-diene,
9-trifluoromethyl-11-formamido-benzo(b)bicyclo[3.3.1]nona-3,6a(10a)-diene.

EXAMPLE VI 8-chloro-11-amino-benzo(b)bicyclo[3.3.1]nona-3,6a(10a)-diene and corresponding N-acyl derivatives The mixture of 11-formamido compounds of Example IV (37 g) is dissolved in ethanol (370 ml) and 10 N aqueous potassium hydroxide solution (37 ml) is added. The solution is refluxed for 4 h, cooled, diluted with water and the crude product isolated using ether. The epimeric mixture is treated with hydrogen chloride in ether and the hydrochlorides chromatographed and fractionally crystallised from methanol yielding 8-chloro-11-anti-amino-benzo(b)bicyclo[3.3.1]nona-3,6a(10a)diene hydrochloride m.p. 235° (6.7 g), and 8-chloro-11-syn-amino-benzo(b)bicyclo[3.3.1]nona-3,6a(10a)-diene hydrochloride m.p. 250° (5.2 g), along with a mixture of epimers (9.0 g) in the mother liquors.

Reaction of the 11-anti-amino compound with acetyl-chloride (1 equivalent) yields the corresponding 8-chloro-11-anti-acetylamino-compound, m.p. 198°–205° C., and with benzoylchloride the corresponding benzoyl derivative (145°–150° C.).

EXAMPLE VII

In the same manner as described in Example VI are prepared the following compounds:
8,9-dichloro-11-syn-amino-benzo(b)bicyclo[3.3.1]nona-3,6a(10a)-diene.HCl,
8,9-dichloro-11-anti-amino-benzo(b)bicyclo[3.3.1]nona-3,6a(10a)-diene.HCl,
9-trifluoromethyl-11-syn-amino-benzo(b)bicyclo[3.3.1]nona-3,6a(10a)-diene.HCl,
8-bromo-11-anti-amino-benzo(b)bicyclo[3.3.1]nona-3,6a(10a)-diene.HCl,
9-chloro-11-syn-amino-benzo(b)bicyclo[3.3.1]nona-3,6a(10a)-diene.HCl,
9-chloro-11-anti-amino-benzo(b)bicyclo[3.3.1]nona-3,6a(10a)-diene.HCl,
8-methyl-11-anti-amino-benzo(b)bicyclo[3.3.1]nona-3,6a(10a)-diene.HCl,
8-methyl-11-syn-amino-benzo(b)bicyclo[3.3.1]nona-3,6a(10a)-diene.HCl,
8-hydroxy-11-syn-amino-benzo(b)bicyclo[3.3.1]nona-3,6a(10a)-diene.HCl,
8-hydroxy-11-anti-amino-benzyl(b)bicyclo[3.3.1]nona-3,6a(10a)-diene.HCl,
8,9-dimethoxy-11-anti-amino-benzo(b)bicyclo[3.3.1]nona-3,6a(10a)-diene.HCl,
8-chloro-9-trifluoromethyl-11-anti-amino-benzo(b)bicyclo[3.3.1]nona-3,6a(10a)-diene,
8-chloro-9-trifluoromethyl-11-syn-amino-benzo(b)bicyclo[3.3.1]nona-3,6a(10a)-diene,
8-nitro-9-trifluoromethyl-11-amino-benzo(b)bicyclo[3.3.1]nona-3,6a(10a)-diene,
8,10-dichloro-11-anti-amino-benzo(b)bicyclo[3.3.1]nona-3,6a(10a)-diene.HCl.

EXAMPLE VIII 11-methylamino-benzo(b)bicyclo[3.3.1]nona-3,6a(10a)-diene

A suspension of lithiumaluminiumhydride (9.24 g) in dry tetrahydrofuran (210 ml) is cautiously and dropwise added to a solution of 11-syn-formamido-benzo(b)bicyclo[3.3.1]nona-3,6a(10a)-diene (35.0 g) in 25 ml dioxan and the resultant mixture stirred at ambient temperature for 5 hours. After addition of water (10 ml), 4 N sodium hydroxide (9 ml) and water (25 ml) the inorganic solids are filtered off. The filtrate is concentrated, diluted with water and the product extracted into ether to give crude 11-syn-methylamino-benzo(b)bicyclo[3.3.1]nona-3,6a(10a)-diene as an oil (35 g). The oily substance is then chromatographed over a silicagel column. Addition of a saturated solution of HCl in ether to an ether solution of the product chromatographed yields a precipitate of 11-syn-methylamino-benzo(b)bicyclo[3.3.1]nona-3,6a(10a)-diene.hydrochloride, which is further purified by repeated crystallisation from methanol/ether. Melting point >260° C.

In the same manner the 11-anti-methylamino salt (HCl) is obtained (subl. p. 270° C.) starting from 11-anti-formamido-benzo(b)bicyclo[3.3.1]nona-3,6a(10a)-diene.

The same product can be obtained by using sodiumcyanoborohydride instead of LiAlH$_4$.

EXAMPLE IX 11-dimethylamino-benzo(b)bicyclo[3.3.1]nona-3,6a(10a)-diene.HCl

A. A solution of 11-syn-methylamino-benzo(b)bicyclo[3.3.1]nona-3,6a(10a)-diene (6.0 g) in a mixture of formic acid (7.0 ml) and formalin (6.5 ml) is heated at 90°–100° C. for 1 h, diluted with water and a slight excess of potassium hydroxide solution, and the product is extracted into ether to give 11-syn-dimethylamino-benzo(b)bicyclo[3.3.1]nona-3,6a(10a)-diene as an oil (6.0 g). Treatment with hydrogen chloride in ether and crystallisation from methanol/ether gives 11-syn-dimethylamino-benzo(b)bicyclo[3.3.1]nona-3,6a(10a)-diene hydrochloride (4.8 g), m.p. >230° C.

In the same manner the corresponding 11-anti-dimethylamino compound is prepared as the HCl salt, m.p. 255° C. (subl.).

B. A mixture of these 11-syn- and 11-anti-dimethylamino compounds is obtained by reacting benzo(b-

)bicyclo[3.3.1]nona-3,6a(10a)-dien-11-one with formic acid and dimethylformamide (instead of formamide) in the same manner as described in Example I. The mixture is chromatographed to give the separate isomers as oily compounds. Treatment with HCl yields the separate HCl salts.

EXAMPLE X 11-syn-dimethylamino-benzo(b)bicyclo[3.3.1]nona-3,6a(10a)-diene.HCl and separation of the optical enantiomers A solution of 11-syn-amino-benzo(b)bicyclo[3.3.1]nona-3,6a(10a)-diene (2.1 g) in a mixture of formic acid (2.4 ml) and formalin (1.7 ml) is heated at 90°–100° C. for 1 h, diluted with water and a slight excess of potassium hydroxide solution and the product is extracted into ether to give 11-syn-dimethylamino-benzo(b)bicyclo[3.3.1]nona-3,6a(10a)-diene as an oil (2.1 g).

Treatment with hydrogenchloride and crystallisation of the product from methanol/ether gives 11-syn-dimethylamino-benzo(b)bicyclo[3.3.1]nona-3,6a(10a)-diene-hydrochloride (1.6 g), m.p. >230°.

The racemic mixture (free base) obtained above is resolved in the usual manner using L-tartaric acid and D-tartaric acid respectively, resulting in the separate (−) and (+) form of 11-syn-dimethylamino-benzo(b)bicyclo[3.3.1]nona-3,6a(10a)-diene. The optical enantiomers are converted into their HCl-salts to obtain crystalline compounds.

EXAMPLE XI 8-methoxy-11-methylamino-benzo(b)bicyclo[3.3.1]nona-3,6a(10a)-diene.HCl 8-methoxy-11-syn-formamido-benzo(b)bicyclo[3.3.1]nona-3,6a(10a)-diene (5.0 g), obtained in Example III is reduced with lithiumaluminiumhydride as described in Example VIII to give 8-methoxy-11-syn-methylamino-benzo(b)bicyclo[3.3.1]nona-3,6a(10a)-diene (4.5 g) which is converted using a saturated solution of hydrogenchloride in ether to the hydrochloride (4.2 g), m.p. 250°–252° C.

In the same manner the 11-anti-methylamino compound is prepared as the HCl salt, m.p. 260° C.

EXAMPLE XII 8-methoxy-11-amino-benzo(b)bicyclo[3.3.1]nona-3,6a(10a)-diene.HCl 8-Methoxy-11-syn-formamido-benzo(b)bicyclo[3.3.1]nona-3,6a(10a)-diene (4.0 g) is hydrolysed with potassium hydroxide solution as described in Example II and the base is treated with hydrogenchloride in ether solution to give 8-methoxy-11-syn-amino-benzo(b)bicyclo[3.3.1]nona-3,6a(10a)-diene.hydrochloride, 3.0 g, m.p. 255°–264° C.

In the same manner the corresponding anti-amino compound is prepared (m.p. HCl salt 240° C.) from the 8-methoxy-11-anti-formamido compound.

EXAMPLE XIII 8-methoxy-11-dimethylamino-benzo(b)bicyclo[3.3.1]nona-3,6a(10a)-diene.HCl 8-Methoxy-11-syn-amino-benzo(b)bicyclo[3.3.1]nona-3,6a(10a)-diene hydrochloride (2.0 g) is treated with sodium hydroxide solution and the free amine is isolated and treated with formic acid and formaldehyde as described in Example X. Treatment of the isolated product with saturated hydrogenchloride in ether gives 8-methoxy-11-syn-dimethylamino-benzo(b)bicyclo[3.3.1]nona-3,6a(10a)-diene hydrochloride (1.7 g) m.p. >205° (decomp.).

In the same manner the 11-anti-dimethylamino compound is prepared as the hydrochloride, melting point 260°–261° C.

EXAMPLE XIV 8-chloro-11-methylamino-benzo(b)bicyclo[3.3.1]nona-3,6a(10a)-diene.HCl A solution of 8-chloro-11-syn and 11-anti-formamidobenzo(b)bicyclo[3.3.1]nona-3,6a(10a)-diene (3.5 g) in dioxan is treated with lithiumaluminiumhydride as described in Example VIII and the epimers separated by fractional crystallisation of their hydrochlorides to give 8-chloro-11-syn-methylamino-benzo(b)bicyclo[3.3.1]nona-3,6a(10a)-diene hydrochloride (1.1 g) m.p. 225° and 8-chloro-11-anti-methylamino-benzo(b)bicyclo[3.3.1]nona-3,6a(10a)-diene hydrochloride (1.0 g) m.p. 220° C.

Reaction of these compounds with an acyl chloride, namely acetylchloride, benzoylchloride, p.chlorobenzoylchloride and phenylpropionylchloride respectively results in the corresponding N-acetyl, N-benzoyl, N-p-chlorobenzoyl and N-phenylpropionyl compound.

EXAMPLE XV 8-chloro-11-dimethylamino-benzo(b)bicyclo[3.3.1]nona-3,6a(10a)-diene and salts A solution of 8-chloro-11-syn-methylamino-benzo(b)bicyclo[3.3.1]nona-3,6a(10a)-diene hydrochloride (0.5 g) is treated with alkali and the free base reacted with formic acid and formaldehyde as described in Example IX. Treatment of the free base with hydrogenchloride yields 8-chloro-11-syn-dimethylamino-benzo(b)bicyclo[3.3.1]nona-3,6a(10a)-diene hydrochloride (0.4 g) m.p. 200° C. Treatment of the free base with maleic acid gives the maleate.

In the same manner the anti-dimethylamino-compound is prepared, melting point HCl salt 193°–198° C., starting from the corresponding 8-chloro-11-anti-methylamino compound.

EXAMPLE XVI

In an analogous manner as described in the Examples VIII, IX and X the following compounds are prepared:
8,9-dichloro-11-syn-methylamino-benzo(b)bicyclo[3.3.1]nona-3,6a(10a)-diene.HCl,
8,9-dichloro-11-anti-methylamino-benzo(b)bicyclo[3.3.1]nona-3,6a(10a)-diene.HCl,
8,9-dichloro-11-syn-dimethylamino-benzo(b)bicyclo[3.3.1]nona-3,6a(10a)-diene.HCl,
8-bromo-11-anti-methylamino-benzo(b)bicyclo[3.3.1]nona-3,6a(10a)-diene.HCl,
8-methyl-11-anti-methylamino-benzo(b)bicyclo[3.3.1]nona-3,6a(10a)-diene.HCl,
8-methyl-11-syn-methylamino-benzo(b)bicyclo[3.3.1]nona-3,6a(10a)-diene.HCl,
8-methyl-11-anti-dimethylamino-benzo(b)bicyclo[3.3.1]nona-3,6a(10a)-diene.HCl,
8-methyl-11-syn-dimethylamino-benzo(b)bicyclo[3.3.1]nona-3,6a(10a)-diene.HCl,
8,9-dimethoxy-11-anti-methylamino-benzo(b)bicyclo[3.3.1]nona-3,6a(10a)-diene.HCl,
9-chloro-11-anti-dimethylamino-benzo(b)bicyclo[3.3.1]nona-3,6a(10a)-diene.HCl, 9-chloro-11-syn-dimethylamino-benzo(b)bicyclo[3.3.1-]nona-3,6a(10a)-diene.HCl,
8-chloro-9-CF$_3$-11-anti-dimethylamino-benzo(b)bicyclo[3.3.1]nona-3,6a(10a)-diene,
8-chloro-9-CF$_3$-11-syn-dimethylamino-benzo(b)bicyclo[3.3.1]nona-3,6a(10a)-diene,
8-nitro-9-CF$_3$-11-dimethylamino-benzo(b)bicyclo[3.3.1]nona-3,6a(10a)-diene,
8,10-dichloro-11-anti-methylamino-benzo(b)bicyclo[3.3.1]nona-3,6a(10a)-diene.HCl.

EXAMPLE XVII 8-methoxy-11-pyrrolidino-benzo(b)bicyclo[3.3.1]nona-3,6a(10a)-diene.HCl 8-Methoxy-benzo(b)bicyclo[3.3.1]nona-3,6a(10a)-diene-11-one (10 g) is treated with formic acid (20 ml) and pyrrolidine (40 ml) in an analogous manner as described in Example I. The crude product is chromatographed over silicagel and the separate fractions are treated with saturated HCl in ether to give 3.5 g 8-methoxy-11-anti-pyrrolidinobenzo(b)bicyclo[3.3.1-]nona-3,6a(10a)-diene.HCl, m.p. >205° C. (dec.), and 1.2 g of the corresponding 11-syn-pyrrolidino- compound, m.p. >195° C. (dec.).

By using other amines instead of pyrrolidine the following compounds are prepared in a similar manner:
8-methoxy-11-syn-piperidino-benzo(b)bicyclo[3.3.1-]nona-3,6a(10a)-diene.HCl,
8-methoxy-11-anti-piperidino-benzo(b)bicyclo[3.3.1-]nona-3,6a(10a)-diene.HCl,
8-methoxy-11-syn-morpholino-benzo(b)bicyclo[3.3.1-]nona-3,6a(10a)-diene.HCl,
8-methoxy-11-anti-morpholino-benzo(b)bicyclo[3.3.1-]nona-3,6a(10a)-diene.HCl,
8-methoxy-11-anti-dimethylamino-benzo(b)bicyclo[3.3.1]nona-3,6a(10a)-diene.maleate and HCl salt,
8-methoxy-11-syn-methylamino-benzo(b)bicyclo[3.3.1-]nona-3,6a(10a)-diene.HCl,
8-methoxy-11-phenylethylamino-benzo(b)bicyclo[3.3.1]nona-3,6a(10a)-diene (oil).

EXAMPLE XVIII

In an analogous manner as described in Example XVII for the preparation of 8-methoxy-substituted benzobicyclononenes, also various unsubstituted benzobicyclononenes can be prepared by reacting benzo(b)bicyclo[3.3.1]nona-3,6a(10a)dien-11-one (10 g) with formic acid and the desired amine of formula III. The mixture of the syn- and anti-amino compound thus obtained is optionally chromatographed over silica and the separate fractions treated with a saturated solution of an organic or inorganic acid in ether or alcohol.

The following compounds are obtained in this manner:
11-syn-dimethylamino-benzo(b)bicyclo[3.3.1]nona-3,6a(10a)-diene.HCl,
11-anti-dimethylamino-benzo(b)bicyclo[3.3.1]nona-3,6a(10a)-diene.HCl,
11-syn-methylamino-benzo(b)bicyclo[3.3.1]nona-3,6a(10a)-diene.HCl,
11-anti-methylamino-benzo(b)bicyclo[3.3.1]nona-3,6a(10a)-diene.HCl,
11-anti-p-hydroxy-phenylethylamino-benzo(b)bicyclo[3.3.1]nona-3,6a(10a)-diene.HCl,
11-syn-p-methoxyphenylethylamino-benzo(b)bicyclo[3.3.1]nona-3,6a(10a)-diene.HCl,
11-anti-N-p-methoxyphenylethyl-N-methylamino-benzo(b)bicyclo[3.3.1]nona-3,6a(10a)-diene.HCl,
11-phenylethylamino-benzo(b)bicyclo[3.3.1]nona-3,6a(10a)-diene (oil),
11-benzylamino-benzo(b)bicyclo[3.3.1]nona-3,6a(10a)-diene (oil).

EXAMPLE XIX

In an analogous manner as described in Example XVII various substituted benzo(b)bicyclo[3.3.1]nona-3,6a(10a)-dien-11-one derivatives are converted into the following compounds using formic acid and an amine as reagents:
8-chloro-11-syn-methylamino-benzo(b)bicyclo[3.3.1-]nona-3,6a(10a)-diene.HCl,
8-chloro-11-anti-methylamino-benzo(b)bicyclo[3.3.1-]nona-3,6a(10a)-diene.HCl,
8-chloro-11-syn-dimethylamino-benzo(b)bicyclo[3.3.1-]nona-3,6a(10a)-diene.HCl,
8-chloro-11-anti-dimethylamino-benzo(b)bicyclo[3.3.1-]nona-3,6a(10a)-diene.HCl,
8-hydroxy-11-syn-dimethylamino-benzo(b)bicyclo[3.3.1]nona-3,6a(10a)-diene.HCl,
8,9-dihydroxy-11-syn-dimethylamino-benzo(b)bicyclo[3.3.1]nona-3,6a(10a)-diene.HCl,
8,9-dimethoxy-11-anti-dimethylamino-benzo(b)bicyclo[3.3.1]nona-3,6a(10a)-diene.HCl,
8,9-dichloro-11-syn-dimethylamino-benzo(b)bicyclo[3.3.1]nona-3,6a(10a)-diene.HCl,
8-bromo-11-anti-methylamino-benzo(b)bicyclo[3.3.1-]nona-3,6a(10a)-diene.HCl,
9-trifluoromethyl-11-dimethylamino-benzo(b)bicyclo[3.3.1]nona-3,6a(10a)-diene,
8,10-dichloro-11-dimethylamino-benzo(b)bicyclo[3.3.1-]nona-3,6a(10a)-diene,
8-chloro-11-anti-ethylamino-benzo(b)bicyclo[3.3.1-]nona-3,6a(10a)-diene,HCl,
8-chloro-11-anti-isopropylamino-benzo(b)bicyclo[3.3.1-]nona-3,6a(10a)-diene.HCl,
8-chloro-11-anti-cyclopentylamino-benzo(b)bicyclo[3.3.1]nona-3,6a(10a)-diene.HCl,
8-chloro-11-anti-pyrrolidino-benzo(b)bicyclo[3.3.1-]nona-3,6a(10a)-diene.HCl.

EXAMPLE XX 11-amino-benzo(b)bicyclo[3.3.1]nona-3,6a(10a)-diene.HCl

A mixture of 0.6 g benzo(b)bicyclo[3.3.1]nona-3,6a(10a)-diene-11-one, 1.5 g hydroxylamine hydrochloride, 18 ml sodiumhydroxide (5%) and 6 ml ethanol is refluxed for 4 hours. The reaction mixture is cooled down and diluted with water. The oily phase is then separated from the aqueous phase and the oily phase is washed twice with water.

The oily substance (the oxime) is then dissolved in isopropanol, after which cautiously and portionwise about 2 g sodium is added. The mixture is stirred until the sodium has been dissolved completely and then further stirred for one additional hour. The reaction mixture is poured into water (300 ml) and extracted with ether. The ether extracts are collected and dried, after which the ether is evaporated, yielding an oily substance consisting of a mixture of the syn- and anti-amino compound. The oily substance is further purified by distillation in vacuo.

The purified oil obtained is dissolved in ether and treated with saturated HCl in ether, yielding a precipitate, that is isolated by filtration. The HCl salt obtained is separated by a careful fractional crystallisation giving the HCl salts of 11-anti- and 11-syn-amino diastereo-isomers in pure state; melting points 265° C. (subl.) and >280° C. respectively.

In the same manner as described in previous examples the 11-amino compound obtained may be alkylated to give the corresponding 11-methylamino and 11-dimethylamino compounds.

In the same manner are prepared:
8-methoxy-11-syn-amino-benzo(b)bicyclo[3.3.1]nona-3,6a(10a)-diene.HCl,
8-methoxy-11-amino-benzo(b)bicyclo[3.3.1]nona-3,6a(10a)-diene.HCl,
8-chloro-11-syn-amino-benzo(b)bicyclo[3.3.1]nona-3,6a(10a)-diene.HCl,
8-chloro-11-anti-amino-benzo(b)bicyclo[3.3.1]nona-3,6a(10a)-diene.HCl,
8,9-dimethoxy-11-syn-amino-benzo(b)bicyclo[3.3.1]nona-3,6a(10a)-diene.HCl,
8,9-dimethoxy-11-anti-amino-benzo(b)bicyclo[3.3.1]nona-3,6a(10a)-diene.HCl,
8-methyl-11-syn-amino-benzo(b)bicyclo[3.3.1]nona-3,6a(10a)-diene.HCl,
8-methyl-11-anti-amino-benzo(b)bicyclo[3.3.1]nona-3,6a(10a)-diene.HCl.

EXAMPLE XXI 11-dimethylamino-benzo(b)bicyclo[3.3.1]nona-3,6a(10a)-diene. HCl

A suspension of LiAlH$_4$ in dry ether is cautiously and dropwise added to a solution of benzo(b)bicyclo[3.3.1]nona-3,6a(10a)-dien-11-one in ether/THF (7:3). The mixture is stirred for 6 hours at ambient temperature. Then water is added to the mixture, after which the mixture is filtered to remove the organic solids. The filtrate is evaporated, and the oily residue washed with water and dried, yielding a crude mixture of both diastereoisomers of 11-hydroxybenzo(b)bicyclo[3.3.1]nona-3,6a(10a)-diene.

4 gram of this crude mixture is dissolved in dry pyridine. The solution is cooled on ice whereupon 5 g tosylchloride is added. The mixture is stirred for 24 hours and then poured into 400 ml water. The aqueous mixture is then extracted into ether and the ether fractions washed with water, 2 n HCl and then washed neutral with water. The ether solution is dried and evaporated, yielding an oily crude mixture of the diastereoisomers of 11-tosyloxy-benzo(b)bicyclo[3.3.1]nona-3,6a(10a)-diene.

To the oily residue obtained, dissolved in dry dimethylsulphoxide (50 ml), 15 ml dimethylamine is added. The mixture is heated on a steambath in a closed ampoule for two hours. The mixture is then cooled, poured into 300 ml water, and extracted into ether. The ether extracts are washed and dried and then treated with saturated solution of HCl in ether. The hydrochlorides obtained are chromatographed over silica and then fractionally crystallised from methanol carefully yielding 11-syn-dimethylamino-benzo(b)bicyclo[3.3.1]nona-3,6a(10a)-diene.HCl, m.p. >230° C., and 11-anti-dimethylamino-benzo(b)bicyclo[3.3.1]nona-3,6a(10a)-diene.HCl, m.p. 255°-259° C. (subl.).

In the same manner are prepared:
8-methoxy-11-anti-pyrrolidino-benzo(b)bicyclo[3.3.1]nona-3,6a(10a)-diene.HCl,
8-methoxy-11-anti-morpholino-benzo(b)bicyclo[3.3.1]nona-3,6a(10a)-diene.HCl,
8-chloro-11-anti-pyrrolidino-benzo(b)bicyclo[3.3.1]nona-3,6a(10a)-diene.HCl,
8-methyl-11-anti-dimethylamino-benzo(b)bicyclo[3.3.1]nona-3,6a(10a)-diene.HCl.

EXAMPLE XXII 11-syn-N-cyclopropylmethylamino-benzo(b)bicyclo[3.3.1]nona-3,6a(10a)-diene.HCl 11-Syn-amino-benzo(b)bicyclo[3.3.1]nona-3,6a(10a)-diene (6.85 g) in toluene (35 ml) is treated with sodium bicarbonate (7.8 g) followed by a solution of cyclopropanecarboxylic acid chloride (4.0 ml) in toluene (35 ml) and the mixture is stirred for 6 h. The mixture is poured into water, allowed to stand for 1 h and the product is isolated using methylene chloride to give 11-syn-cyclopropane carboxamido-benzo(b)bicyclo[3.3.1]nona-3,6a(10a)-diene (7.2 g).

A suspension of LiAlH$_4$ (1.6 g) in dry tetrahydrofuran (30 ml) is dropwise added to a stirred solution of 7.2 g of the above product, dissolved in 60 ml warm tetrahydrofuran, after which the reaction mixture is stirred for 20 h. The mixture is then cooled and water (6 ml), sodium hydroxide solution (6 ml; 4 N) and water (18 ml) are added. The mixture is filtered, the filtrate diluted with water and the product isolated by extracting with ether. The ether is evaporated and the residue dissolved and chromatographed over silica.

Treatment of the residue after removal of solvent with a saturated solution of hydrogen chloride in ether given 11-syn-N-cyclopropylmethylamino-benzo(b)bicyclo[3.3.1]nona-3,6a(10a)-diene.HCl, melting point >230° C.

In a similar manner the following compounds are prepared:
8-chloro-11-anti-N-cyclopropylmethylamino-benzo(b)bicyclo[3.3.1]nona-3,6a(10a)-diene.HCl,
8-chloro-11-anti-N-ethylamino-benzo(b)bicyclo[3.3.1]nona-3,6a(10a)-diene hydrochloride,
8-methoxy-11-syn-N-cyclopropylmethylamino-benzo(b)bicyclo[3.3.1]nona-3,6a(10a)-diene.HCl,
11-syn-N-p-methoxyphenethylamino-benzo(b)bicyclo[3.3.1]nona-3,6a(10a)-diene.HCl,
11-anti-N-p-hydroxyphenethylamino-benzo(b)bicyclo[3.3.1]nona-3,6a(10a)-diene.HCl,
8-chloro-11-anti-N-p-methoxyphenethylamino-benzo(b)bicyclo[3.3.1]nona-3,6a(10a)-diene.HCl.

Starting from the appropriate 11-methylamino derivatives the following compounds are prepared in a similar manner:
11-anti-N-cyclopropylmethyl-N-methylamino-benzo(b)bicyclo[3.3.1]nona-3,6a(10a)-diene hydrochloride,
11-syn-N-cyclopropylmethyl-N-methylamino-benzo(b)bicyclo[3.3.1]nona-3,6a(10a)-diene citrate, and the corresponding HCl salt,
11-anti-N-p-methoxyphenethyl-N-methylamino-benzo(b)bicyclo[3.3.1]nona-3,6a(10a)-diene.HCl,
11-anti-N-p-hydroxyphenethyl-N-methylamino-benzo(b)bicyclo[3.3.1]nona-3,6a(10a)-diene.HCl,
11-syn-N-p-chlorophenethyl-N-methylamino-benzo(b)bicyclo[3.3.1]nona-3,6a(10a)-diene.HCl,
11-anti-N-p-chlorophenethyl-N-methylamino-benzo(b)bicyclo[3.3.1]nona-3,6a(10a)-diene.HCl.

EXAMPLE XXIII 11-syn-N-p-hydroxyphenethyl-N-methylamino-benzo(b)bicyclo[3.3.1]nona-3,6a(10a)-diene.HCl 11-Syn-N-p-methoxyphenethyl-N-methylamino-benzo(b)bicyclo[3.3.1]-nona-3,6a(10a)-diene hydrochloride (4.12 g) was added to fused pyridine hydrochloride (25 g) at 170°–210° C. and the mixture was stirred for 30 min. The solution was cooled, water (25 ml) was added followed by solid sodium bicarbonate (1.1 g). The precipitated solid was filtered off, washed with a little water and re-crystallised from methanol/ether to give 11-syn-N-p-hydroxyphenethyl-N-methylamino-benzo(b)bicyclo[3.3.1]nona-3,6a(10a)-diene hydrochloride 2.41 g, m.p. 260°–266° C.

EXAMPLE XXIV 8-hydroxy-11-syn-dimethylamino-benzo(b)bicyclo[3.3.1]nona-3,6a(10a)-diene.HCl 8-Methoxy-11-syn-dimethylamino-benzo(b)bicyclo[3.3.1]nona-3,6a(10a)-diene.hydrochloride (11 g) is heated with fused pyridine hydrochloride (87 g) at 170°–220° C. under nitrogen for 15 min, whereupon the mixture is cooled and water is added. The pH is adjusted to 12 addition of solid sodium bicarbonate and the product is isolated using methylene chloride and treated with a saturated solution of hydrogen chloride in methylene chloride to give 8-hydroxy-11-syn-dimethylamino-benzo(b)bicyclo[3.3.1]nona-3,6a(10a)-diene.HCl, melting point >240° C.

The following compounds are prepared in a similar manner:
8-hydroxy-11-syn-amino-benzo(b)bicyclo[3.3.1]nona-3,6a(10a)-diene hydrochloride,
8-hydroxy-11-anti-amino-benzo(b)bicyclo[3.3.1]nona-3,6a(10a)-diene hydrochloride.

We claim:

1. A method for treating depression in humans, which comprises administering orally to a human requiring treatment for depression a pharmaceutical composition comprising:
   (A) a pharmaceutically antidepressant effective amount of a compound of the formula:

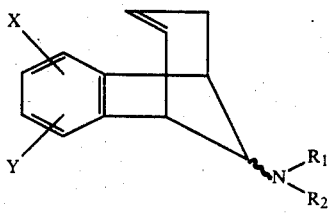

or a pharmaceutically acceptable salt thereof, in which
   $R_1$ is selected from the group consisting of hydrogen and alkyl hydrocarbons of one to six carbon atoms;
   $R_2$ is an aralkyl group that is an alkyl moiety of one to six carbon atoms and substituted with at least one aromatic group; and
   X and Y are each selected from the group consisting of hydrogen, hydroxy, halogen, alkyl of one to six carbon atoms, alkoxy of one to six carbon atoms, nitro, and trifluoromethyl; and
   (B) a pharmaceutically effective carrier
   whereby the composition is a solid dosage unit selected from the group consisting of a pill, a tablet, a coated tablet, and a capsule.

2. A pharmaceutical composition having anorectic properties comprising:
   (A) an anorectically effective amount of a compound of the formula:

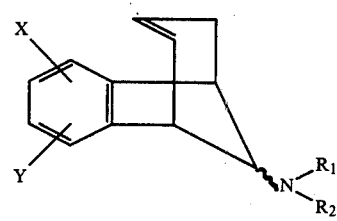

or a pharmaceutically acceptable salt thereof, in which
   $R_1$ is selected from the group consisting of hydrogen and alkyl hydrocarbon of one to six carbon atoms;
   $R_2$ is an aralkyl group that is an alkyl moiety of one to six carbon atoms and substituted with at least one aromatic group; and
   X and Y are each selected from the group consisting of hydrogen, hydroxy, halogen, alkyl of one to six carbon atoms, alkoxy of one to six carbon atoms, nitro, and trifluoromethyl; and
   (B) a pharmaceutically effective carrier whereby the composition is a solid dosage unit selected from the group consisting of a pill, a tablet, a coated tablet, and a capsule.

3. The composition of claim 2 wherein said compound is 8-methoxy-11-phenylethylamino-benzo(b)bicyclo[3.3.1]nona-3,6a(10a)-diene.

4. The composition of claim 2 wherein said compound is 11-anti-p-hydroxy-phenyl-ethylamin-benzo(b)bicyclo[3.3.1]nona-3,6a(10a)-diene.

5. The composition of claim 2 wherein said compound is 11-syn-p-methoxyphenyl-ethyl-amino-benzo(b)bicyclo[3.3.1]-nona-3,6a(10a)-diene.

6. The composition of claim 2 wherein said compound is 11-phenylethylamino-benzo(b)bicyclo[3.3.1]nona-3,6a(10a)-diene.

7. The composition of claim 2 wherein said compound is 11-benzylamino-benzo(b)bicyclo[3.3.1]nona-3,6a(10)-diene.

* * * * *

UNITED STATES PATENT OFFICE
CERTIFICATE OF CORRECTION

Patent No. 4,264,626           Dated April 28, 1981

Inventor(s) Colin Leslie Hewett and David S. Savage

It is certified that error appears in the above-identified patent and that said Letters Patent are hereby corrected as shown below:

In Col. 1, about lines 50-55, correct formula II as follows:

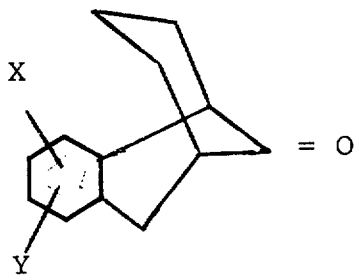

In Col. 7, lines 23-24, correct the spelling of "4-endo-hydroxy-benzo(b)bicyclo[3.3.1]nonan-11-one".

In Col. 12, lines 31-32, correct the spelling of "8-chloro-11-syn-methylamino-benzo(b)bicyclo-[3.3.1]nona-3,6a(10a)-diene".

In Col. 13, lines 47-48, correct the spelling of "benzo(b)-bicyclo[3.3.1]nona-3,6a(10a)-dien-11-one".

In Col. 16, lines 55-56, correct the spelling of "11-anti-N-cyclopropylmethyl-N-methylamino-benzo(b)bicyclo[3.3.1]nona-3,6a(10a)-diene".

In Col. 16, lines 65-66, correct the spelling of "11-syn-N-p-chlorophenethyl-N-methylamino-benzo(b)bicyclo[3.3.1]nona-3,6a(10a)-diene".

UNITED STATES PATENT OFFICE
CERTIFICATE OF CORRECTION

Patent No. 4,264,626   Dated April 28, 1981

Inventor(s) Colin Leslie Hewett and Davis S. Savage

It is certified that error appears in the above-identified patent and that said Letters Patent are hereby corrected as shown below:

In Col. 16, lines 67-68, correct the spelling of "11-anti-N-p-chlorophenethyl-N-methylamino-benzo(b)bicyclo[3.3.1]nona-3,6a(10a)-diene".

In Claim 3, correct the spelling of "8-methoxy-11-phenylethyl-amino-benzo(b)cicyclo[3.3.1]nona-3,6a(10a)-diene".

In Claim 4, correct the spelling of "11-anti-p-hydroxyphenyl-ethylamin-benzo(b)bicyclo-[3.3.1]nona-3,6a(10a)-diene".

Signed and Sealed this

Twenty-ninth Day of September 1981

[SEAL]

Attest:

Attesting Officer

GERALD J. MOSSINGHOFF

Commissioner of Patents and Trademarks